US011969277B2

(12) United States Patent
Pang et al.

(10) Patent No.: US 11,969,277 B2
(45) Date of Patent: Apr. 30, 2024

(54) FLAT PANEL DETECTOR, DRIVING METHOD THEREOF AND DETECTION DEVICE

(71) Applicants: Beijing BOE Sensor Technology Co., Ltd., Beijing (CN); BOE Technology Group Co., Ltd., Beijing (CN)

(72) Inventors: Fengchun Pang, Beijing (CN); Xuecheng Hou, Beijing (CN); Jinyu Li, Beijing (CN); Zhenwu Jiang, Beijing (CN)

(73) Assignees: Beijing BOE Sensor Technology Co., Ltd., Beijing (CN); BOE Technology Group Co., Ltd., Beijing (CN)

( * ) Notice: Subject to any disclaimer, the term of this patent is extended or adjusted under 35 U.S.C. 154(b) by 367 days.

(21) Appl. No.: 17/516,180

(22) Filed: Nov. 1, 2021

(65) Prior Publication Data

US 2022/0296186 A1    Sep. 22, 2022

(30) Foreign Application Priority Data

Mar. 19, 2021   (CN) .......................... 202110298025.4

(51) Int. Cl.
*G09G 3/20*   (2006.01)
*A61B 6/42*   (2024.01)
*A61B 6/50*   (2024.01)
(52) U.S. Cl.
CPC ............ *A61B 6/4233* (2013.01); *A61B 6/502* (2013.01); *G09G 3/20* (2013.01); *G09G 2310/0267* (2013.01); *G09G 2310/0297* (2013.01)

(58) Field of Classification Search
CPC ........ A61B 6/4233; A61B 6/502; G09G 3/20; G09G 2310/0267; G09G 2310/0297
See application file for complete search history.

(56) References Cited

U.S. PATENT DOCUMENTS 11,640,807 B2 *   5/2023   Kobayashi ............ G06F 1/1652
                                                                 345/87

FOREIGN PATENT DOCUMENTS

JP            2016059041 A  *  4/2016   ........... G09G 3/3225

* cited by examiner

*Primary Examiner* — David P Porta
*Assistant Examiner* — Fani Polyzos Boosalis
(74) *Attorney, Agent, or Firm* — IPro, PLLC (57) ABSTRACT

The present disclosure discloses a flat panel detector, a driving method thereof and a detection device. The flat panel detector includes: at least one stage of first demultiplexer, wherein signal output terminals of a first stage of first demultiplexer are connected with the scanning signal lines in one-to-one correspondence, signal output terminals of other stage of first demultiplexer serves as signal input terminals of the previous stage of first demultiplexer, the first demultiplexers are configured to provide signals of the signal input terminals to all the signal output terminals in time division, the signal input terminals and the signal output terminals included in the different stages of first demultiplexers differ from one another, and the quantity of the signal input terminals and the quantity of the signal output terminals are reduced stage by stage from the first stage of first demultiplexer to the last stage of first demultiplexer.

20 Claims, 8 Drawing Sheets

FLAT PANEL DETECTOR, DRIVING METHOD THEREOF AND DETECTION DEVICE

CROSS REFERENCE TO RELATED APPLICATIONS

The present disclosure claims priority to Chinese Patent Application No. 202110298025.4 filed with the China National Intellectual Property Administration on Mar. 19, 2021, the entire contents of which are incorporated herein by its reference.

FIELD

The present disclosure relates to the technical field of digital medical imaging, in particular to a flat panel detector, a driving method thereof and a detection device.

BACKGROUND

In a field of digital medical imaging, an X-ray flat panel detector is popularly applied.

An existing breast-type X-ray flat panel detector has a higher requirement for a spatial resolution, thereby being small in pixel size. Besides, one side of the breast-type X-ray flat panel detector is usually required to be a narrow frame, which is generally within 1.5 mm, consequently, a bonding region of leads for bonding is unavailable on the one side with the narrow frame, and thus a breast product needs to be bonded on a single side. As a result of a limited wiring space of the flat panel detector, a large quantity of leads needing to be externally connected and a small pin width of the bonding region, a bonding technique is difficult, and the cost is high.

SUMMARY

Embodiments of the present disclosure provide a flat panel detector, a driving method thereof and a detection device.

In a first aspect, an embodiment of the present disclosure provides a flat panel detector, divided into a detection region and a peripheral region surrounding the detection region, and including: a plurality of scanning signal lines, located in the detection region and divided into a plurality of groups; and at least one stage of first demultiplexer, located in a portion of the peripheral region on one side of the detection region, wherein signal output terminals of a first stage of first demultiplexer are connected with the scanning signal lines in one-to-one correspondence, signal output terminals of another stage of first demultiplexer serves as signal input terminals of the previous stage of first demultiplexer, a current stage of first demultiplexer is configured to provide signals of the signal input terminals of the current stage of first demultiplexer to the signal output terminals of the current stage of first demultiplexer in time division, and a quantity of the signal input terminals and a quantity of the signal output terminals are reduced stage by stage from the first stage of first demultiplexer to the last stage of first demultiplexer.

In some embodiments, each stage of first demultiplexer is uniformly divided into a plurality of first repetitive circuits, each of the first repetitive circuits includes a plurality of first transistors, gates of the first transistors in one first repetitive circuit are electrically connected with one same first signal selection terminal, first electrodes of the first transistors in one first repetitive circuit are electrically connected with different signal input terminals of a current stage of first demultiplexer, and second electrodes of the first transistors in one first repetitive circuit serve as the signal output terminals of the current stage of first demultiplexer.

In some embodiments, in each stage of first demultiplexer, different first repetitive circuits are connected with different first signal selection terminals, respectively, and a quantity of the first repetitive circuits included in one stage of first demultiplexer is the same as a quantity of the first signal selection terminals included in the one stage of first demultiplexer.

In some embodiments, for one stage of first demultiplexer, a quantity of the first transistors included in each of the first repetitive circuits is the same, and a quantity of the first transistors included in one first repetitive circuit is the same as a quantity of the signal input terminals of the one stage of first demultiplexer.

In some embodiments, scanning signal lines electrically connected with the second electrodes of the plurality of first transistors included in one first repetitive circuit in the first stage of first demultiplexer are arranged continuously.

In some embodiments, the flat panel detector further includes: a second demultiplexer, wherein the second demultiplexer is divided into a plurality of second repetitive circuits, each of the second repetitive circuits includes a plurality of second transistors, gates of the second transistors in one second repetitive circuit are electrically connected with one same second signal selection terminal, first electrodes of the second transistors in the second repetitive circuits are electrically connected with one same signal input terminal of the second demultiplexer, second electrodes of the second transistors in one second repetitive circuit serve as the signal output terminals of the second demultiplexer, the one same signal input terminal of the second demultiplexer is connected with a specified voltage source, the second repetitive circuits in the second demultiplexer are in one-to-one correspondence with the first repetitive circuits in the first stage of first demultiplexer, and the second transistors in the second repetitive circuits are in one-to-one correspondence with the first transistors in the corresponding first repetitive circuits in the first stage of first demultiplexer.

In some embodiments, different second repetitive circuits are connected with different second signal selection terminals, respectively, and a quantity of the second repetitive circuits is the same as a quantity of the second signal selection terminals.

In some embodiments, a quantity of the second transistors included in each of the second repetitive circuits is the same, and the second demultiplexer is configured to provide specified voltage making detection pixels connected to the corresponding scanning signal lines stop working for the signal output terminals of the first repetitive circuits, not outputting signals to the scanning signal lines, in the first stage of first demultiplexer.

In a second aspect, an embodiment of the present disclosure provides a driving method of a flat panel detector, including: controlling each stage of demultiplexer in all stages of first demultiplexers to be turned on in time division, so that signals received by signal input terminals of a current stage of first demultiplexer are provided to signal output terminals of the current stage of first demultiplexer in time division.

In some embodiments, the driving method further includes: controlling second repetitive circuits in a second demultiplexer corresponding to first repetitive circuits not turned on in the first stage of first demultiplexer in a condition that any one of the first repetitive circuits in the first stage of first demultiplexer is turned on, so as to make detection pixels on scanning signal lines corresponding to the first repetitive circuits not turned on stop working.

In a third aspect, an embodiment of the present disclosure provides a detection device, including the flat panel detector as described in the first aspect, and a driving chip bonded with a peripheral region of the flat panel detector through a flexible printed circuit board.

DETAILED DESCRIPTION OF THE EMBODIMENTS

Embodiments of the present disclosure provide a flat panel detector, a driving method thereof and a detection device for solving above problems in the prior art.

In order to make above objectives, features and advantages of the present disclosure clearer and more understandable, the present disclosure will be further described in combination with accompanying drawings and the embodiments. However, the exemplary implementations may be implemented in various modes instead of being constructed as limitation to the described implementations herein. Rather, these implementations are provided to make the present disclosure more comprehensive and complete, and the concept of the exemplary implementations is fully conveyed to those skilled in the art. Same reference numerals in the drawings denote the same or similar structures whose repeated descriptions are omitted. All described words for representing positions and directions in the present disclosure are described by taking the drawings for example, and changes may also be made as required within the protection scope of the present disclosure. The drawings of the present disclosure are only intended to denote a relative position relation but not a true scale.

It should be noted that specific details are set forth in the following description for the sake of fully understanding the present disclosure. The present disclosure may be implemented in other various modes different from the modes described herein, and those skilled in the art may make similar promotion without departing from the intension of the present disclosure. Therefore, the present disclosure is not limited by the specific implementations disclosed below. The following descriptions in the specification are preferred implementations for implementing the present application and are only intended to set forth general principles of the present application but not to limit the scope of the present application. The protection scope of the present application shall be as defined by the appended claims.

In combination with the drawings, the flat panel detector, the driving method thereof and the detection device provided by the embodiments of the present disclosure are described in detail as follows.

Figure 1:
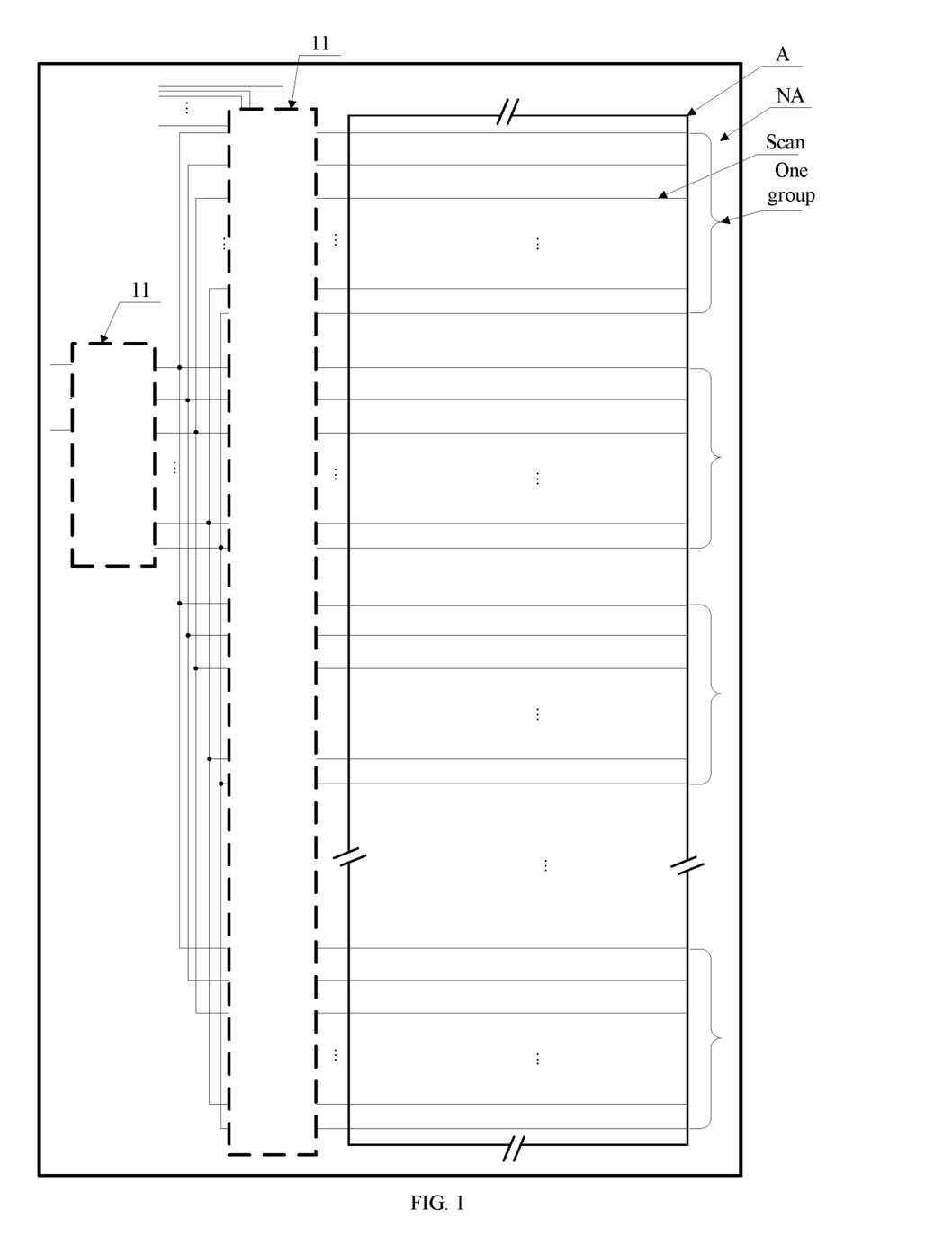
FIG. 1 is a schematic structural diagram of a flat panel detector provided by an embodiment of the present disclosure.

FIG. 1 is a schematic structural diagram of a flat panel detector provided by an embodiment of the present disclosure. The flat panel detector is divided into a detection region A and a peripheral region NA surrounding the detection region A, and includes: a plurality of scanning signal lines Scan and at least one stage of first demultiplexer 11.

The plurality of scanning signal lines Scan is located in the detection region A and divided into a plurality of groups (multiple scanning signal lines Scan included in a brace serve "}" as one group in FIG. 1).

At least one stage of first demultiplexer 11 is located in the peripheral region NA (a region surrounded by a bold frame except the detection region A in FIG. 1) on one side of the detection region A. The respective signal output terminals of a first stage of first demultiplexer 11 are connected with the respective scanning signal lines Scan in one-to-one correspondence, signal output terminals of another stage of first demultiplexer 11 serves as signal input terminals of the previous stage of first demultiplexer 11, and the first demultiplexer 11 is configured to provide signals of the signal input terminals to the signal output terminals in time division; and a quantity of the signal input terminals and a quantity of the signal output terminals are different in different stages of first demultiplexers 11, and the quantity of the signal input terminals and the quantity of the signal output terminals are reduced stage by stage from the first stage of first demultiplexer 11 to the last stage of first demultiplexer 11.

It should be understood that FIG. 1 shows the two stages of first demultiplexers 11, thus the previous stage of first demultiplexer 11 of the another stage of first demultiplexer 11 (equivalently, the second stage of first demultiplexer 11 in the two stages of first demultiplexers 11 shown in FIG. 1) is the first stage of first demultiplexer 11, and the signal output terminal of the second stage of first demultiplexer 11 serve as the signal input terminal of the first stage of first demultiplexer 11 in FIG. 1.

In the embodiment provided by the present disclosure, the signals of the signal input terminals are provided to all the signal output terminals in time division through the at least one stage of above first demultiplexer 11, so that the quantity of leads connected into the at least one stage of first demultiplexer 11 may be greatly reduced. Bonding regions corresponding to the leads are disposed on one side of the detection region, and other side may be provided with a narrow frame, so that the flat panel detector may be suitable for a detection demand of breast-type imaging.

Figure 2:
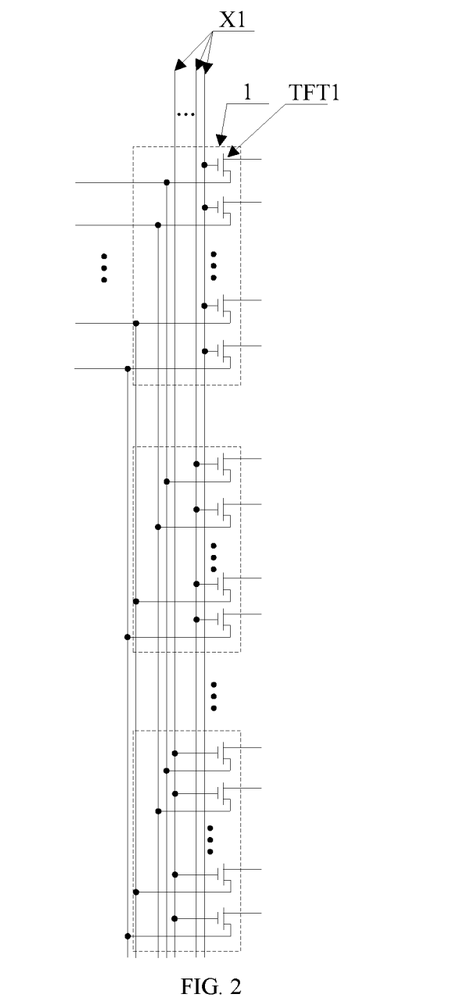
FIG. 2 is a schematic structural diagram of a first demultiplexer provided by an embodiment of the present disclosure.

FIG. 2 is a schematic structural diagram of the first demultiplexer provided by some embodiments of the present disclosure. The first demultiplexer 11 is uniformly divided into a plurality of first repetitive circuits 1. One first repetitive circuit 1 includes a plurality of first transistors TFT1, gates of all the first transistors TFT1 in one first repetitive circuit 1 are electrically connected with the one same first signal selection terminal X1, first electrodes of all the first transistors TFT1 in one first repetitive circuit 1 are electrically connected with the different signal input terminals of the first demultiplexer 11, and second electrodes of all the first transistors TFT1 in one first repetitive circuit 1 serve as all the signal output terminals of the first demultiplexer 11.

In the first demultiplexer 11, the different first repetitive circuits 1 are connected with the different first signal selection terminals X1, respectively, and the quantity of the first repetitive circuits 1 included in the first demultiplexer 11 is the same as the quantity of the first signal selection terminals included in the first demultiplexer 11.

The quantity of the first transistors TFT1 included in each of the first repetitive circuits 1 is the same, and the quantity of the first transistors TFT1 included in one first repetitive circuit 1 is the same as the quantity of the signal input terminals of the first demultiplexer 11.

In FIG. 2, the first demultiplexer 11 includes M signal input terminals, N signal output terminals, K first signal selection terminals X1 and totally K first repetitive circuits 1. First electrodes of all the first transistors TFT1 in these K first repetitive circuits 1 are electrically connected with the different signal input terminals of the first demultiplexer 11, so that the K first repetitive circuits 1 may share the signal input terminals of the first demultiplexer 11. Gates of all the first transistors TFT1 in the one same first repetitive circuit 1 are connected with the one same first signal selection terminal, the different first repetitive circuits 1 are connected with the different first signal selection terminals, by sending a first selection signal to all the first signal selection terminals in time division, the K first repetitive circuits 1 in the first demultiplexer 11 may be controlled to use the signal input terminals of the first demultiplexer 11 in time division to transmit signals to corresponding signal output terminals, and thus the quantity of the signal input terminals of the first demultiplexer 11 is reduced.

Figure 3:
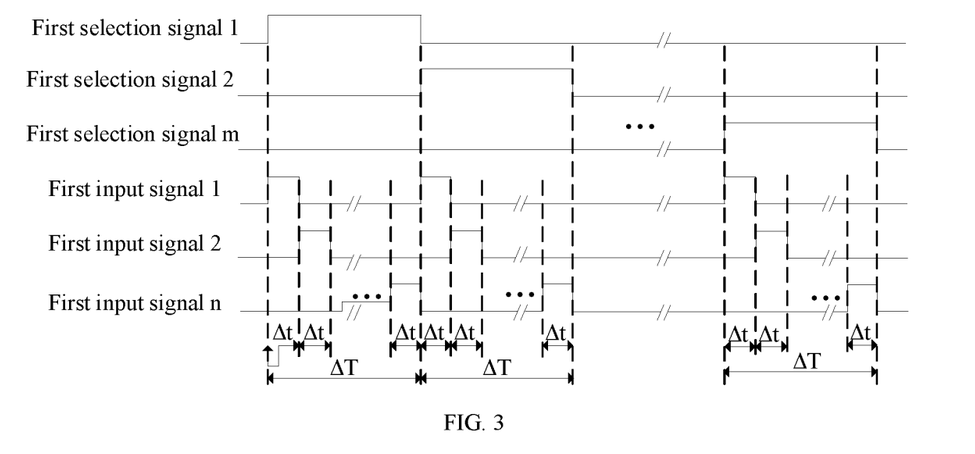
FIG. 3 is a sequence diagram of a first demultiplexer provided by an embodiment of the present disclosure.

FIG. 3 is a sequence diagram of the first demultiplexer provided by an embodiment of the present disclosure.

Hypothetically, the first demultiplexer 11 in FIG. 2 includes m first repetitive circuits 1, first selection signals received by the first signal selection terminals corresponding to the m first repetitive circuits 1 are a first selection signal 1 to a first selection signal m in sequence, the quantity of the signal input terminals of the first demultiplexer 11 is n, first input signals received by the n signal input terminals are a first input signal 1 to a first input signal n in sequence, and the first demultiplexer 11 includes m×n signal output terminals. Hypothetically, the first transistors TFT1 in the first repetitive circuits 1 are N-type transistors.

Please refer to FIG. 3, when a first first repetitive circuit 1 receives an active first selection signal 1 (namely, a high level signal), the respectively corresponding first input signal 1 to the first input signal n (active high) are received from the n signal input terminals of the first demultiplexer 11, and the first input signal 1 to the first input signal n are output to the signal output terminals of the first first repetitive circuit 1.

When a second first repetitive circuit 1 receives an active first selection signal 2 (namely, a high level signal), the respectively corresponding first input signal 1 to the first input signal n (active high) are received from the n signal input terminals of the first demultiplexer 11, and the first input signal 1 to the first input signal n are output to the signal output terminals of the second first repetitive circuit 1.

When an $m^{th}$ first repetitive circuit 1 receives an active first selection signal m (namely, a high level signal), the respectively corresponding first input signal 1 to the first input signal n (active high) are received from the n signal input terminals of the first demultiplexer 11, and the first input signal 1 to the first input signal n are output to the signal output terminals of the $m^{th}$ first repetitive circuit 1.

It should be noted that a duration of a high level of each of the first selection signal 1 to the first selection signal m is $\Delta T$, and a duration of a high level of each of the first input signal 1 to the first input signal n is $\Delta t$, wherein $\Delta T=n\times\Delta t$. The first transistors TFT1 in FIG. 2 may also be P-type transistors. When the first thin film transistor TFT1 in FIG. 2 are P-type transistors, thin film transistors connected to the scanning signal lines and controlling detection pixels to work are P-type transistors as well, correspondingly, the first input signal 1 to the first input signal n, and the first selection signal 1 to the first selection signal m are active low, and the corresponding sequence diagram also needs to be adjusted correspondingly.

Figure 4:
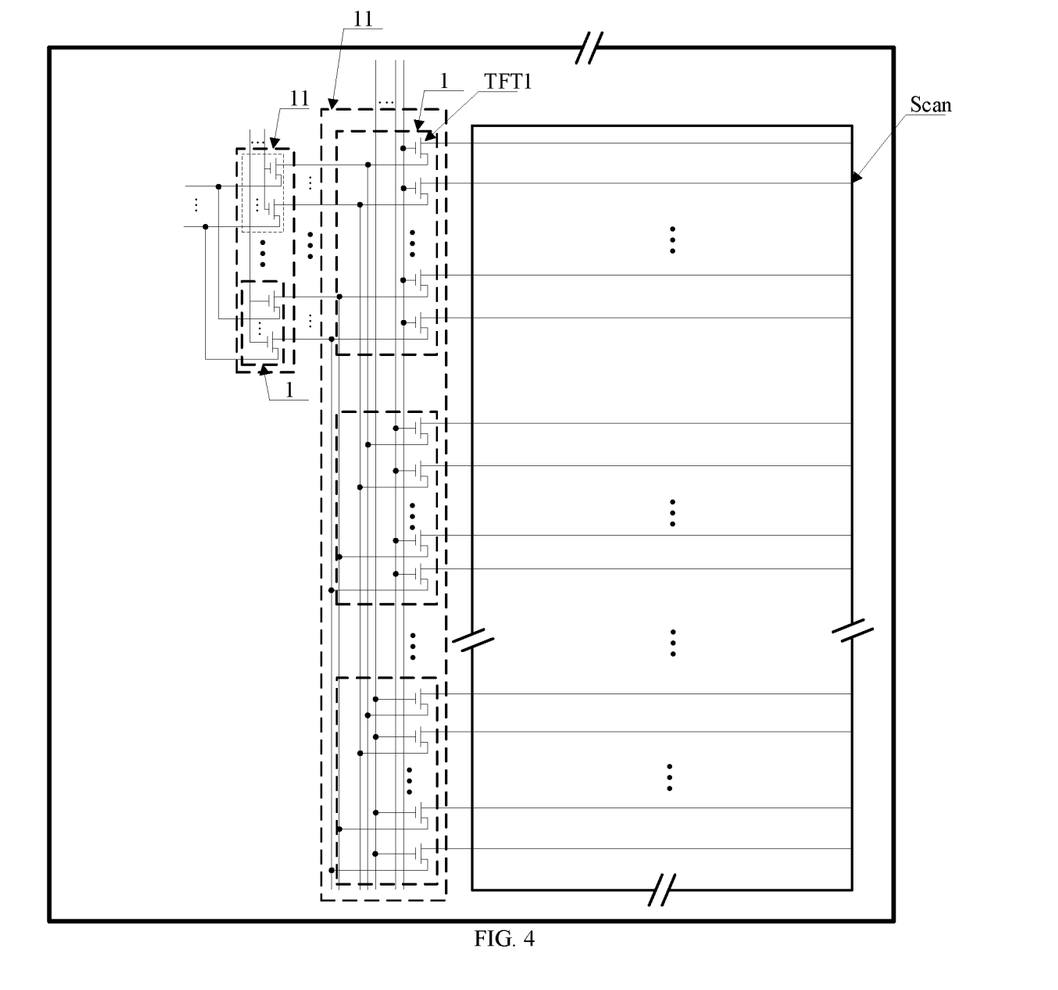
FIG. 4 is a schematic structural diagram of another flat panel detector provided by an embodiment of the present disclosure.

FIG. 4 is a schematic structural diagram of another flat panel detector provided by an embodiment of the present disclosure.

Hypothetically, in FIG. 4, the quantity of the scanning signal lines included in the flat panel detector is n, the first stage of first demultiplexer 11 (namely, the first demultiplexer 11 the signal output terminals of which are directly connected with the scanning signal lines) includes the m first repetitive circuits 1, the total quantity of the first signal selection terminals included in the first stage of first demultiplexer 11 is m, the total quantity of the signal input terminals is n/m, and the quantity of the signal input terminals and the quantity of the signal output terminals of the respective first repetitive circuits 1 in the first stage of first demultiplexer 11 are n/m. The signal output terminals of the second stage of first demultiplexer 11 are connected with the signal input terminals of the first stage of first demultiplexer 11 in one-to-one correspondence. Hypothetically, the second stage of first demultiplexer 11 includes i first repetitive circuits 1, and the total quantity of the first signal selection terminals included in the second stage of first demultiplexer 11 is i as well. Hypothetically, the total quantity of the signal input terminals included in the second stage of first demultiplexer 11 is j, and j=n/m/i.

Signals received by the first signal selection terminals included in the first stage of first demultiplexer 11 are marked as a first selection signal 11 to a first selection signal 1m in sequence, signals received by the first signal selection terminals included in the second stage of first demultiplexer 11 are marked as a first selection signal 21 to a first selection signal 2i in sequence, and signals received by the signal input terminals included in the second stage of first demultiplexer 11 are marked as a first input signal 2i to a first input signal 2j in sequence. The sequence diagram corresponding to FIG. 4 refers to FIG. 5 which is a sequence diagram of two stages of first demultiplexers provided by an embodiment of the present disclosure.

Figure 5:
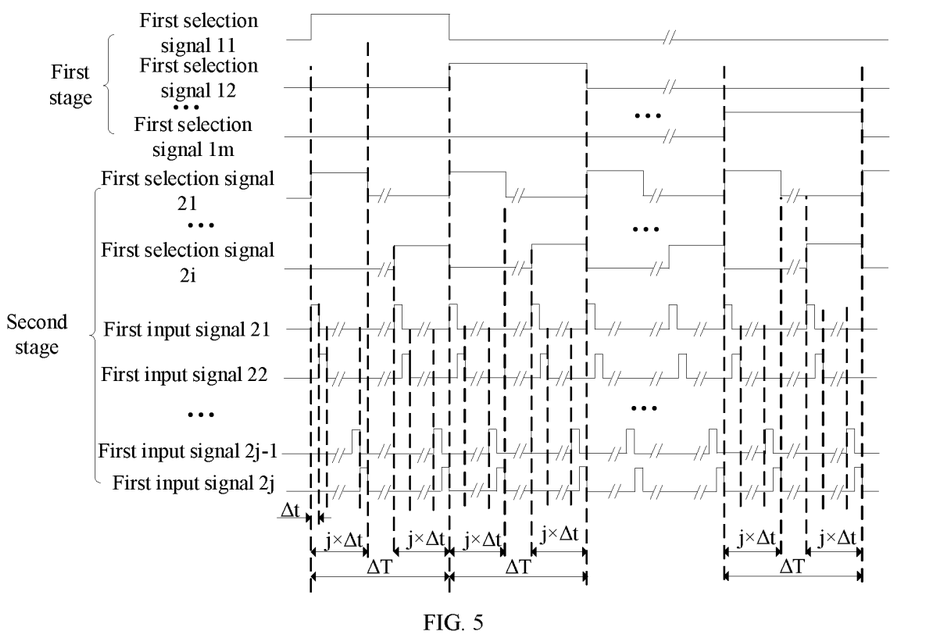
FIG. 5 is a sequence diagram of two stages of first demultiplexers provided by an embodiment of the present disclosure.

In FIG. 5, a duration of high level signals received by the signal input terminals of the second stage of first demultiplexer 11 is $\Delta t$, a duration of each high level signal in the first selection signal 21 to the first selection signal 2i received by the first signal selection terminals of the second stage of first demultiplexer 11 is $j\times\Delta t$, a duration of each high level signal in the first selection signal 11 to the first selection signal 1m received by the first stage of first demultiplexer 11 is $\Delta T=i\times j\times\Delta t$, and a duration needed for completing one-time scanning of the n scanning signal lines of the flat panel detector is mx $\Delta T$.

It should be noted that the at least one stage of first demultiplexer 11 may also be disposed at the first signal selection terminals included in the first demultiplexer 11, thus the quantity of to-be-introduced leads of the first signal selection terminals is reduced, and a disposing mode is similar to a mode of disposing at least one stage of first demultiplexer 11 on one side of the scanning signal line and is not repeated herein.

Figure 6:
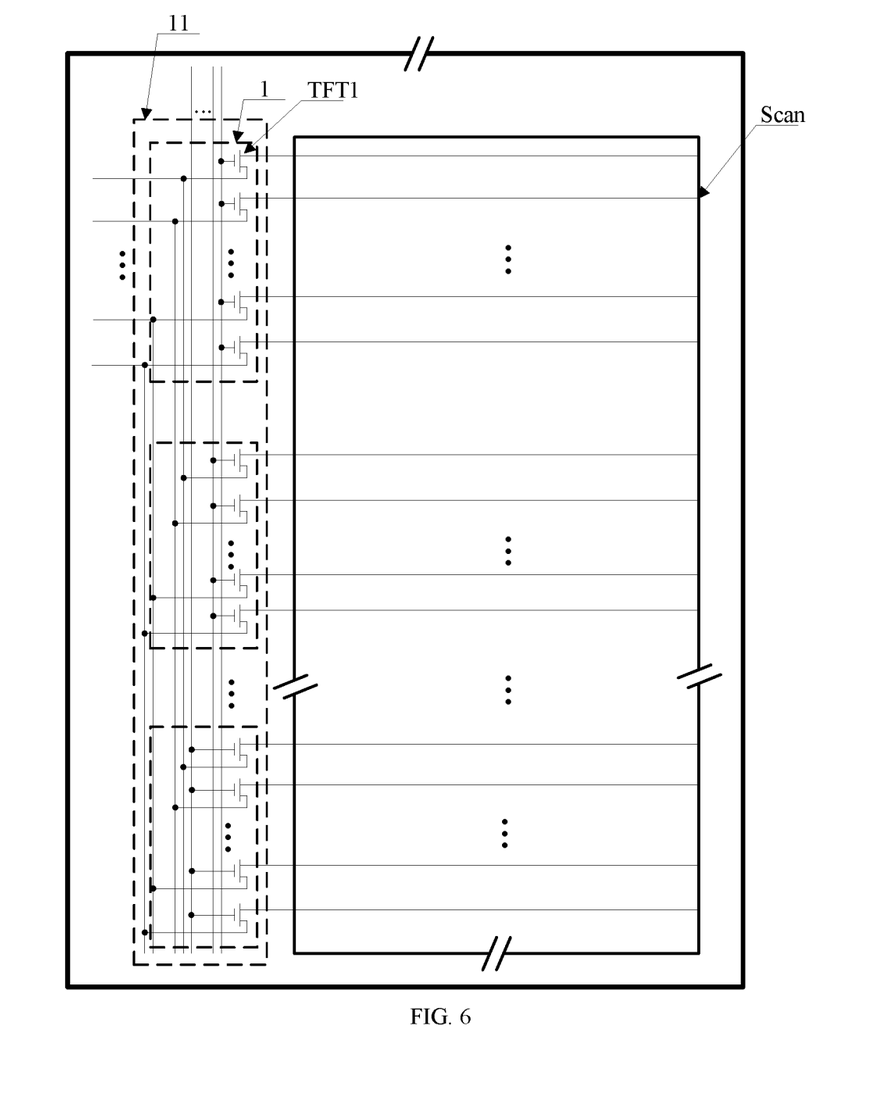
FIG. 6 is a schematic structural diagram of further flat panel detector provided by an embodiment of the present disclosure.

FIG. 6 is a schematic structural diagram of further flat panel detector provided by an embodiment of the present disclosure. In FIG. 6, for example, the flat panel detector includes only the first stage of first demultiplexer 11.

The scanning signal lines Scan electrically connected with the second electrodes of the plurality of first transistors TFT1 included in one first repetitive circuit 1 in the first stage of first demultiplexer 11 are arranged continuously.

When the flat panel detector includes a plurality of stages of first demultiplexers 11, a connection mode of the first stage of first demultiplexer 11 with the scanning signal lines Scan is the same as FIG. 3.

In the embodiment provided by the present disclosure, the scanning signal lines Scan electrically connected with the second electrodes of the plurality of first transistors TFT1 included in one first repetitive circuit 1 in the first stage of first demultiplexer 11 are arranged continuously, so that scanning signals corresponding to all the scanning signal lines Scan are conveniently transmitted to the corresponding scanning signal lines Scan row by row when the first repetitive circuits 1 are controlled in time division.

Figure 7:
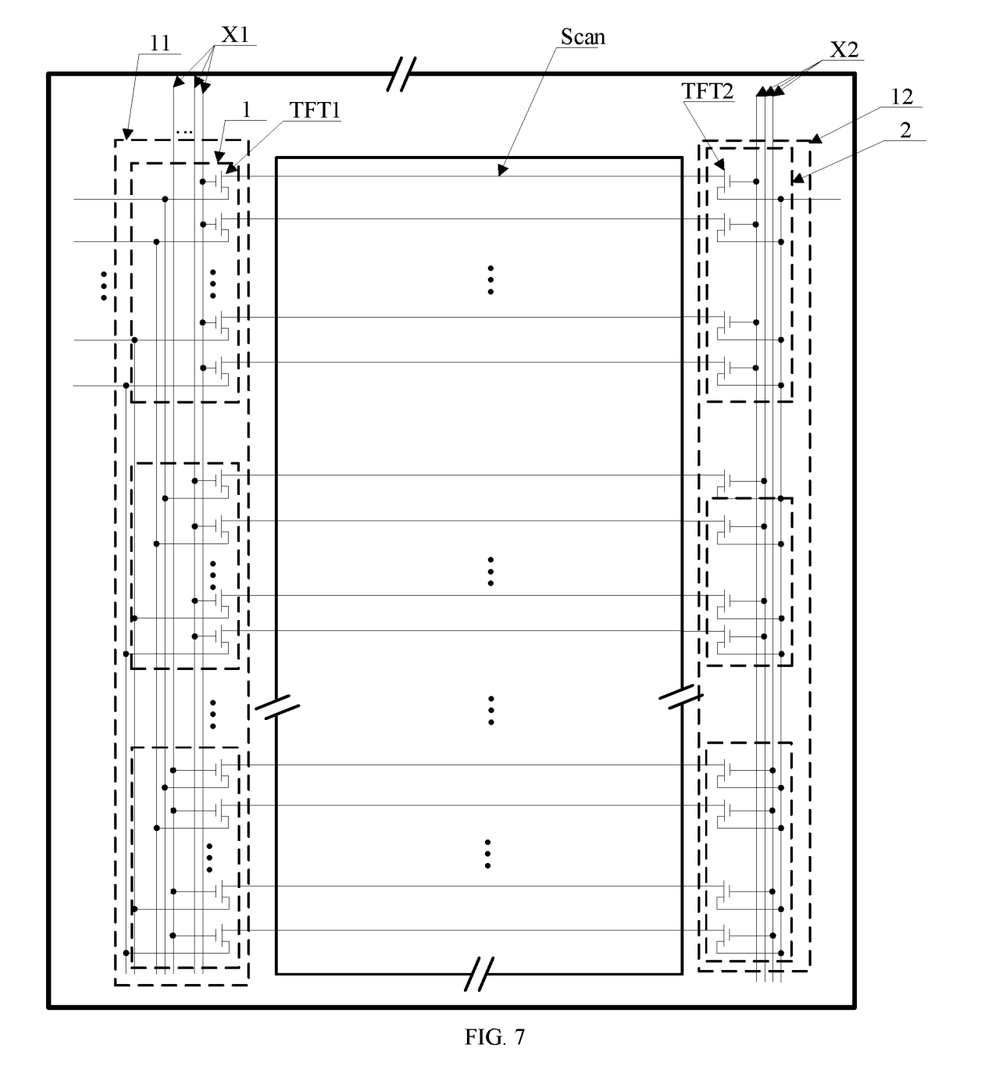
FIG. 7 is a schematic structural diagram of yet another flat panel detector provided by an embodiment of the present disclosure.

FIG. 7 is a schematic structural diagram of yet another flat panel detector provided by an embodiment of the present disclosure.

The flat panel detector further includes: a second demultiplexer 12. The second demultiplexer 12 is divided into a plurality of second repetitive circuits 2, one second repetitive circuit 2 includes a plurality of second transistors TFT2, gates of all the second transistors TFT2 in one second repetitive circuit 2 are electrically connected with the one same second signal selection terminal X2, first electrodes of all the second transistors TFT2 in all the second repetitive circuits 2 are electrically connected with the one same signal input terminal of the second demultiplexer 12, and second electrodes of all the second transistors TFT2 in one second repetitive circuit 2 serve as all the signal output terminals of the second demultiplexer 12.

It should be noted that in FIG. 7, for the sake of convenient seeing, the second demultiplexer 12 and the first demultiplexer 11 are disposed on different sides of the detection region A. During actual application, the second demultiplexer 12 and the first demultiplexer 11 may be disposed on the same side of the detection region A, so that a narrow frame may be conveniently realized on one side of the detection region A.

The different second repetitive circuits 2 are connected with the different second signal selection terminals X2, respectively, and the quantity of the second repetitive circuits 2 is the same as the quantity of the second signal selection terminals.

The quantity of the second transistors TFT2 included in each of the second repetitive circuits 2 is the same. The signal input terminals of the second demultiplexer 12 are electrically connected with a specified voltage terminal. The second demultiplexer 12 is configured to provide specified voltage making detection pixels (not shown in the figure) connected to the corresponding scanning signal lines Scan stop working for the signal output terminals of the first repetitive circuits 1, not outputting signals to the scanning signal lines Scan, in the first stage of first demultiplexer 11.

In FIG. 7, for example, the detection pixels connected to each of the scanning signal lines Scan are controlled by the N-type transistors to work or not, the specified voltage is low voltage. In FIG. 6, the first first repetitive circuit 1 in the first stage of first demultiplexer 11 uses the signal input terminals of the current stage of first demultiplexer 11 to receive scanning signals at present, the scanning signals are transmitted to the corresponding row of scanning signal line Scan, the other second repetitive circuits 2 except for the first second repetitive circuit 2 (corresponding to the first first repetitive circuit 1) in the second demultiplexer 12 receive the second selection signals through the respective second signal selection terminals X2 for gating of the corresponding second repetitive circuits 2, thus all the second repetitive circuits 2 except for the first second repetitive circuit 2 apply a low voltage signal to the signal output terminals of the corresponding first repetitive circuits 1, so that the detection pixels connected to the corresponding scanning signal lines stop working. In this way, it may be guaranteed that only the detection pixels on the scanning signal line corresponding to the first first repetitive circuit 1 may work at present, and reading errors of detection signal data are avoided.

Figure 8:
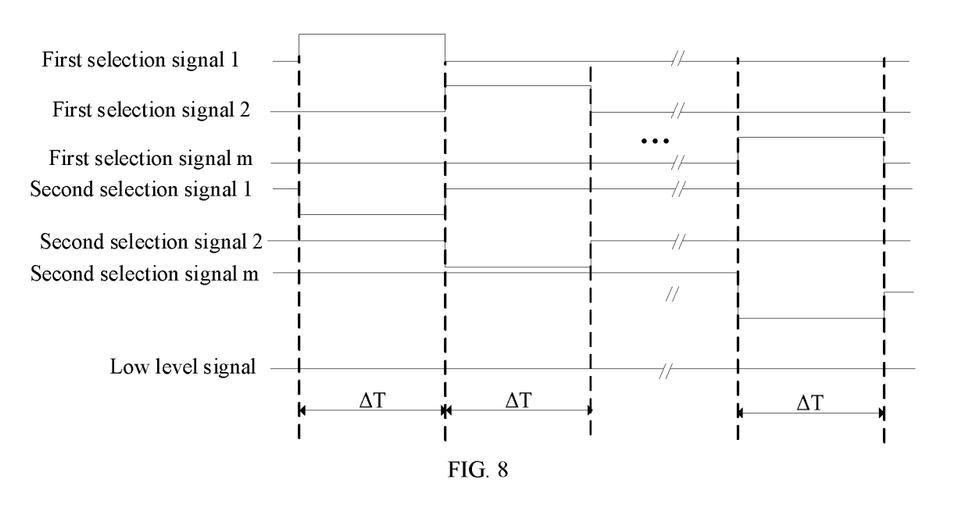
FIG. 8 is a sequence diagram of a second demultiplexer provided by an embodiment of the present disclosure.

FIG. 8 is a sequence diagram of the second demultiplexer provided by an embodiment of the present disclosure.

Hypothetically, in FIG. 7, the first stage of first demultiplexer 11 includes m first repetitive circuits 1, the first selection signals received by the first signal selection terminals corresponding to the m first repetitive circuits 1 are the first selection signal 1 to the first selection signal m in sequence, the quantity of the signal input terminals of the first stage of first demultiplexer 11 is n, the first input signals received by the n signal input terminals are the first input signal 1 to the first input signal n in sequence, and the first stage of first demultiplexer 11 includes m×n signal output terminals.

Correspondingly, the second demultiplexer 12 also includes m second repetitive circuits 2, the second selection signals received by second signal selection terminals corresponding to the m second repetitive circuits 2 are a second selection signal 1 to a second selection signal m in sequence, the quantity of the signal input terminals of the second demultiplexer 12 is also n, the second input signals received by the n signal input terminals are a second input signal 1 to a second input signal n in sequence, and the second demultiplexer 12 includes m×n signal output terminals.

Hypothetically, the first transistors TFT1 in the first repetitive circuits 1 and the second transistors TFT2 in the second repetitive circuits 2 are both N-type transistors. The first first repetitive circuit 1 to the $m^{th}$ first repetitive circuit 1 are in one-to-one correspondence with the first second repetitive circuit 2 to the $m^{th}$ second repetitive circuit 2. Correspondingly, the first first transistor TFT1 to the $n^{th}$ first transistor TFT1 in the first repetitive circuits 1 are also in one-to-one correspondence with the first second transistor TFT2 to the $n^{th}$ second transistor TFT2 in the second repetitive circuits 2.

Please continue referring to FIG. 8, when the first first repetitive circuit 1 receives an active first selection signal 1 (namely, a high level signal), the first second repetitive circuit 2 receives an inactive second selection signal 1 (a low level signal is identified as inactive), the other second repetitive circuits 2 receive active second selection signals (the second selection signal 2 to the second selection signal m, active high), so that the other second repetitive circuits 2 except for the first second repetitive circuit 2 are turned on, low level signals (hypothetically, control signals needed for working of the detection pixels are high level signals) received by the signal input terminals of the second demultiplexer 12 are transmitted to the corresponding scanning signal lines, and the detection pixels on these scanning signal lines stop working. In FIG. 8, the signal input terminals of the second demultiplexer 12 only need to be connected with a lower voltage terminal (e.g., a ground terminal).

When the second first repetitive circuit 1 receives an active first selection signal 2 (namely, the high level signal), the second second repetitive circuit 2 receives an inactive second selection signal 2 (a low level signal is identified as inactive), the other second repetitive circuits 2 receive active second selection signals (active high), so that the other second repetitive circuits 2 except for the second second repetitive circuit 2 are turned on, the low level signals received by the signal input terminals of the second demultiplexer 12 are transmitted to the corresponding scanning signal lines, and thus the detection pixels on these scanning signal lines stop working.

When the $m^{th}$ first repetitive circuit 1 receives an active first selection signal m (namely, the high level signal), the $m^{th}$ second repetitive circuit 2 receives an inactive second selection signal m (a low level signal is identified as inactive), the other second repetitive circuits 2 receive active second selection signals (active high), so that the other second repetitive circuits 2 except for the $m^{th}$ second repetitive circuit 2 is turned on, the low level signals received by the signal input terminals of the second demultiplexer 12 are transmitted to the corresponding scanning signal lines, and the detection pixels on these scanning signal lines stop working.

Based on the same inventive concept, an embodiment of the present disclosure provides a driving method of a flat panel detector, including: each stage of first demultiplexer in all stages of first demultiplexers is controlled to be turned on in time division, so that signals received by signal input terminals of a current stage of first demultiplexer are provided to all signal output terminal of the current stage of first demultiplexer in time division.

In some embodiments, the driving method further includes: second repetitive circuits in a second demultiplexer corresponding to first repetitive circuits not turned on in a first stage of first demultiplexer are controlled to be turned on when any one of the first repetitive circuits in the first stage of first demultiplexer is turned on so as to make detection pixels on scanning signal lines corresponding to the first repetitive circuits not turned on stop working.

Based on the same inventive concept, an embodiment of the present disclosure provides a detection device, including the flat panel detector as described above, and a driving chip bonded with a peripheral region of the flat panel detector through a flexible printed circuit board.

The detection device may be an X-ray detection device applicable to breast imaging detection.

Though the preferred embodiments of the present disclosure have been described, those skilled in the art may make extra changes and modifications for these embodiments once they know the basic inventive concept. Thus, the appended claim intends to be constructed as including the preferred embodiments and all these changes and modifications falling within the scope of the present disclosure.

Apparently, those skilled in the art may make various changes and modifications without departing from the spirit and scope of the present disclosure. In this case, if these changes and modifications of the present disclosure fall within the scope of the claims and their equivalents, the present disclosure also intends to include these changes and modifications.

What is claimed is:

1. A flat panel detector, divided into a detection region and a peripheral region surrounding the detection region, and comprising:
    a plurality of scanning signal lines, located in the detection region and divided into a plurality of groups; and
    at least one stage of first demultiplexer, located in a portion of the peripheral region on one side of the detection region, wherein signal output terminals of a first stage of first demultiplexer are connected with the scanning signal lines in one-to-one correspondence, signal output terminals of another stage of first demultiplexer serves as signal input terminals of the previous stage of first demultiplexer, a current stage of first demultiplexer is configured to provide signals of the signal input terminals of the current stage of first demultiplexer to the signal output terminals of the current stage of first demultiplexer in time division, and a quantity of the signal input terminals and a quantity of the signal output terminals are reduced stage by stage from the first stage of first demultiplexer to the last stage of first demultiplexer.

2. The flat panel detector according to claim 1, wherein each stage of first demultiplexer is uniformly divided into a plurality of first repetitive circuits, each of the first repetitive circuits comprises a plurality of first transistors, gates of the first transistors in one first repetitive circuit are electrically connected with one same first signal selection terminal, first electrodes of the first transistors in one first repetitive circuit are electrically connected with different signal input terminals of a current stage of first demultiplexer, and second electrodes of the first transistors in one first repetitive circuit serve as the signal output terminals of the current stage of first demultiplexer.

3. The flat panel detector according to claim 2, wherein in each stage of first demultiplexer, different first repetitive circuits are connected with different first signal selection terminals, respectively, and a quantity of the first repetitive circuits comprised in one stage of first demultiplexer is the same as a quantity of the first signal selection terminals comprised in the one stage of first demultiplexer.

4. The flat panel detector according to claim 3, wherein for one stage of first demultiplexer, a quantity of the first transistors comprised in each of the first repetitive circuits is the same, and a quantity of the first transistors comprised in one first repetitive circuit is the same as a quantity of the signal input terminals of the one stage of first demultiplexer.

5. The flat panel detector according to claim 4, wherein scanning signal lines electrically connected with the second electrodes of the plurality of first transistors comprised in one first repetitive circuit in the first stage of first demultiplexer are arranged continuously.

6. The flat panel detector according to claim 5, further comprising:
    a second demultiplexer, wherein the second demultiplexer is divided into a plurality of second repetitive circuits, each of the second repetitive circuits comprises a plurality of second transistors, gates of the second transistors in one second repetitive circuit are electrically connected with one same second signal selection terminal, first electrodes of the second transistors in the second repetitive circuits are electrically connected with one same signal input terminal of the second demultiplexer, and second electrodes of the second transistors in one second repetitive circuit serve as the signal output terminals of the second demultiplexer.

7. The flat panel detector according to claim 6, wherein: the one same signal input terminal of the second demultiplexer is connected with a specified voltage source, the second repetitive circuits in the second demultiplexer are in one-to-one correspondence with the first repetitive circuits in the first stage of first demultiplexer, and the second transistors in the second repetitive circuits are in one-to-one correspondence with the first transistors in the corresponding first repetitive circuits in the first stage of first demultiplexer.

8. The flat panel detector according to claim 4, further comprising:
a second demultiplexer, wherein the second demultiplexer is divided into a plurality of second repetitive circuits, each of the second repetitive circuits comprises a plurality of second transistors, gates of the second transistors in one second repetitive circuit are electrically connected with one same second signal selection terminal, first electrodes of the second transistors in the second repetitive circuits are electrically connected with one same signal input terminal of the second demultiplexer, and second electrodes of the second transistors in one second repetitive circuit serve as the signal output terminals of the second demultiplexer.

9. The flat panel detector according to claim 8, wherein: the one same signal input terminal of the second demultiplexer is connected with a specified voltage source, the second repetitive circuits in the second demultiplexer are in one-to-one correspondence with the first repetitive circuits in the first stage of first demultiplexer, and the second transistors in the second repetitive circuits are in one-to-one correspondence with the first transistors in the corresponding first repetitive circuits in the first stage of first demultiplexer.

10. The flat panel detector according to claim 3, further comprising:
a second demultiplexer, wherein the second demultiplexer is divided into a plurality of second repetitive circuits, each of the second repetitive circuits comprises a plurality of second transistors, gates of the second transistors in one second repetitive circuit are electrically connected with one same second signal selection terminal, first electrodes of the second transistors in the second repetitive circuits are electrically connected with one same signal input terminal of the second demultiplexer, and second electrodes of the second transistors in one second repetitive circuit serve as the signal output terminals of the second demultiplexer.

11. The flat panel detector according to claim 10, wherein: the one same signal input terminal of the second demultiplexer is connected with a specified voltage source, the second repetitive circuits in the second demultiplexer are in one-to-one correspondence with the first repetitive circuits in the first stage of first demultiplexer, and the second transistors in the second repetitive circuits are in one-to-one correspondence with the first transistors in the corresponding first repetitive circuits in the first stage of first demultiplexer.

12. The flat panel detector according to claim 2, further comprising:
a second demultiplexer, wherein the second demultiplexer is divided into a plurality of second repetitive circuits, each of the second repetitive circuits comprises a plurality of second transistors, gates of the second transistors in one second repetitive circuit are electrically connected with one same second signal selection terminal, first electrodes of the second transistors in the second repetitive circuits are electrically connected with one same signal input terminal of the second demultiplexer, and second electrodes of the second transistors in one second repetitive circuit serve as the signal output terminals of the second demultiplexer.

13. The flat panel detector according to claim 12, wherein: the one same signal input terminal of the second demultiplexer is connected with a specified voltage source, the second repetitive circuits in the second demultiplexer are in one-to-one correspondence with the first repetitive circuits in the first stage of first demultiplexer, and the second transistors in the second repetitive circuits are in one-to-one correspondence with the first transistors in the corresponding first repetitive circuits in the first stage of first demultiplexer.

14. The flat panel detector according to claim 12, wherein a quantity of the second transistors comprised in each of the second repetitive circuits is the same, and the second demultiplexer is configured to provide specified voltage making detection pixels connected to the corresponding scanning signal lines stop working for the signal output terminals of the first repetitive circuits, not outputting signals to the scanning signal lines, in the first stage of first demultiplexer.

15. The flat panel detector according to claim 12, wherein different second repetitive circuits are connected with different second signal selection terminals, respectively, and a quantity of the second repetitive circuits is the same as a quantity of the second signal selection terminals.

16. A driving method, wherein the driving method is used for driving the flat panel detector according to claim 1, and the driving method comprises:
controlling each stage of demultiplexer in all stages of first demultiplexers to be turned on in time division, so that signals received by signal input terminals of a current stage of first demultiplexer are provided to signal output terminals of the current stage of first demultiplexer in time division.

17. The driving method according to claim 16, further comprising:
controlling second repetitive circuits in a second demultiplexer corresponding to first repetitive circuits not turned on in the first stage of first demultiplexer in a condition that any one of the first repetitive circuits in the first stage of first demultiplexer is turned on, so as to make detection pixels on scanning signal lines corresponding to the first repetitive circuits not turned on stop working.

18. A detection device, comprising the flat panel detector according to claim 1, and a driving chip bonded with a peripheral region of the flat panel detector through a flexible printed circuit board.

19. The detection device according to claim 18, wherein the detection device is an X-ray detection device.

20. The detection device according to claim 18, wherein the detection device is used for breast imaging detection.

* * * * *